(12) United States Patent
Henley et al.

(10) Patent No.: US 9,345,834 B2
(45) Date of Patent: May 24, 2016

(54) AUTOINJECTOR

(71) Applicant: SANOFI-AVENTIS DEUTSCHLAND GMBH, Frankfurt am Main (DE)

(72) Inventors: Thomas Henley, Biggleswade (GB); David Cross, Hertfordshire (GB); Douglas Ivan Jennings, Herts (GB); Ryan Anthony McGinley, Cambridge (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 14/360,291

(22) PCT Filed: Nov. 23, 2012

(86) PCT No.: PCT/EP2012/073468
§ 371 (c)(1),
(2) Date: May 22, 2014

(87) PCT Pub. No.: WO2013/076247
PCT Pub. Date: May 30, 2013

(65) Prior Publication Data
US 2014/0323978 A1    Oct. 30, 2014

(30) Foreign Application Priority Data

Nov. 24, 2011    (EP) .................................. 11190592

(51) Int. Cl.
*A61M 5/20*    (2006.01)
*A61M 5/31*    (2006.01)
(Continued)

(52) U.S. Cl.
CPC ............... *A61M 5/3148* (2013.01); *A61M 5/20* (2013.01); *A61M 5/2033* (2013.01); *A61M 5/322* (2013.01); *A61M 5/3213* (2013.01);
(Continued)

(58) Field of Classification Search
CPC ............ A61M 5/20; A61M 2005/202; A61M 5/2033; A61M 5/31578; A61M 2005/206; A61M 5/31571; A61M 5/322; A61M 5/3243; A61M 5/31565; A61M 5/31566; A61M 5/315351; A61M 5/3234
See application file for complete search history.

(56) References Cited

U.S. PATENT DOCUMENTS

| 6,270,479 B1 | 8/2001 | Bergens et al. |
| 6,312,412 B1 | 11/2001 | Saied et al. |
| 6,371,939 B2 * | 4/2002 | Bergens et al. ............... 604/156 |

FOREIGN PATENT DOCUMENTS

| EP | 2364741 | 9/2011 |
| WO | 2009/098502 | 8/2009 |

(Continued)

OTHER PUBLICATIONS

International Search Report for Int. App. No. PCT/EP2012/073468, completed Feb. 15, 2013.

*Primary Examiner* — Kami A Bosworth
*Assistant Examiner* — Nilay Shah
(74) *Attorney, Agent, or Firm* — Fish & Richardson P.C.

(57) ABSTRACT

Described is an autoinjector comprising a case, a drive carriage disposed in the case, and a plunger coupled to the drive carriage. The plunger is adapted to releasably engage a needle retraction mechanism in a syringe. Translation of the drive carriage in a distal direction relative to the case causes the plunger to engage the needle retraction mechanism and translation of the drive carriage in a proximal direction relative to the casing case the plunger to needle retraction mechanism the stopper.

12 Claims, 13 Drawing Sheets

(51) Int. Cl.
 A61M 5/46 (2006.01)
 A61M 5/315 (2006.01)
 A61M 5/32 (2006.01)
 A61M 5/24 (2006.01)

(52) U.S. Cl.
 CPC .............. *A61M 5/3234* (2013.01); *A61M 5/46* (2013.01); A61M 5/31515 (2013.01); A61M 5/3204 (2013.01); A61M 5/326 (2013.01); A61M 2005/202 (2013.01); A61M 2005/206 (2013.01); A61M 2005/208 (2013.01); A61M 2005/2026 (2013.01); A61M 2005/2407 (2013.01); A61M 2005/2481 (2013.01); A61M 2005/2492 (2013.01); A61M 2005/3231 (2013.01); A61M 2005/3236 (2013.01); A61M 2005/3267 (2013.01); A61M 2205/581 (2013.01); A61M 2205/582 (2013.01); A61M 2205/584 (2013.01)

(56) References Cited

FOREIGN PATENT DOCUMENTS

| WO | 2011/075760 | 6/2011 |
| WO | 2011/101380 | 8/2011 |

\* cited by examiner

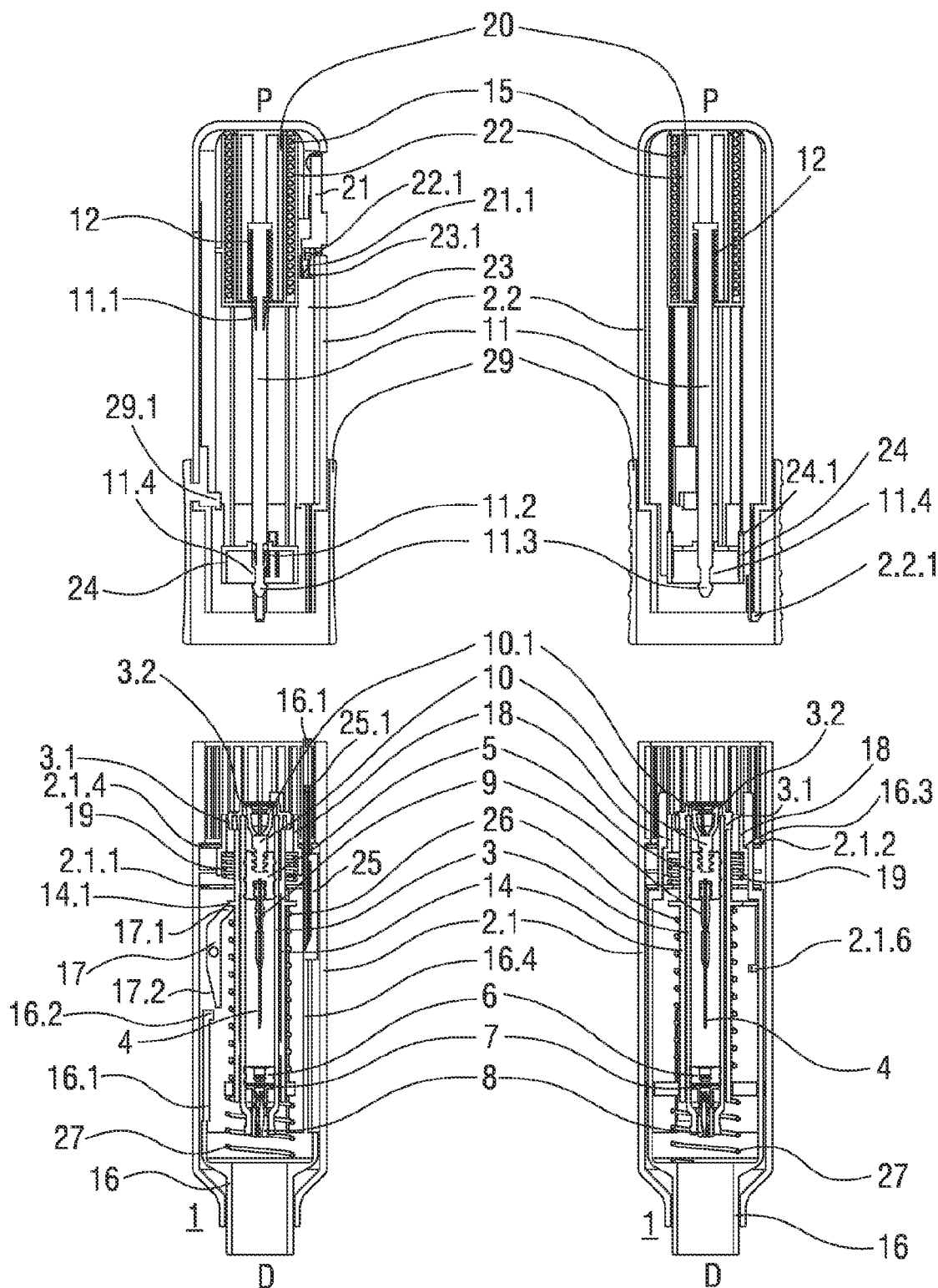

AUTOINJECTOR

CROSS REFERENCE TO RELATED APPLICATIONS

The present application is a U.S. National Phase Application pursuant to 35 U.S.C. §371 of International Application No. PCT/EP2012/073468 filed Nov. 23, 2012, which claims priority to European Patent Application No. 11190592.3 filed Nov. 24, 2011. The entire disclosure contents of these applications are herewith incorporated by reference into the present application.

TECHNICAL FIELD

The invention relates to an autoinjector for administering a medicament.

BACKGROUND

Administering an injection is a process which presents a number of risks and challenges for users and healthcare professionals, both mental and physical.

Injection devices typically fall into two categories— manual devices and autoinjectors. In a conventional manual device, a user must provide force to drive a medicament through a needle. This is typically done by some form of button/plunger that has to be continuously pressed during the injection. There are numerous disadvantages for the user from this approach. For example, if the user stops pressing the button/plunger, the injection will stop and may not deliver an intended dose to a patient. Further, the force required to push the button/plunger may be too high for the user (e.g., if the user is elderly). And, aligning the injection device, administering the injection and keeping the injection device still during the injection may require dexterity which some patients (e.g., elderly patients, children, arthritic patients, etc.) may not have.

Autoinjector devices aim to make self-injection easier for patients. A conventional autoinjector may provide the force for administering the injection by a spring, and trigger button or other mechanism may be used to activate the injection. Autoinjectors may be single-use or reusable devices.

There remains a need for an improved autoinjector.

SUMMARY

It is an object of the present invention to provide a novel syringe and novel reusable autoinjector for operating the syringe.

In an exemplary embodiment, an autoinjector according to the present invention comprises a case, a drive carriage disposed in the case, and a plunger coupled to the drive carriage. The plunger is adapted to releasably engage a needle retraction mechanism in a syringe. Translation of the drive carriage in a distal direction relative to the case causes the plunger to engage the needle retraction mechanism and translation of the drive carriage in a proximal direction relative to the casing case the plunger to needle retraction mechanism the stopper.

In an exemplary embodiment, the autoinjector further comprises a drive spring biasing the drive carriage relative to the case.

In an exemplary embodiment, the autoinjector further comprises a plunger spring biasing the plunger relative to the drive carriage.

In an exemplary embodiment, the plunger includes proximal resilient arms adapted to engage a distal aperture in the drive carriage.

In an exemplary embodiment, the autoinjector further comprises a latch tube coupled to the plunger. The latch tube includes resilient arms. The plunger includes distal resilient arms adapted to engage a proximal aperture in the latch tube. When the drive carriage abuts the latch tube, the proximal resilient arms are deflected by the proximal aperture in the latch tube and the plunger translates in the proximal direction relative to the drive carriage under a force of the plunger spring.

In an exemplary embodiment, the case includes a stem adapted to engage a proximal end of the plunger. When the drive carriage separates from the latch tube, the drive carriage and the plunger translate in the proximal direction relative to the case until the stem engages the distal end of the plunger and prevents the plunger from further translation while allowing further translation of the drive carriage. The further translation of the drive carriage causes the proximal resilient arms to deflect and re-engage the distal aperture of the drive carriage.

In an exemplary embodiment, the autoinjector further comprises an interlock sleeve slidably disposed in the case, and a sleeve spring adapted to apply a biasing force to the interlock sleeve relative to the case.

In an exemplary embodiment, the autoinjector further comprises a latch sleeve slidably disposed in the case, and a latch sleeve spring adapted to apply a biasing force to the latch sleeve relative to the case. When the interlock sleeve translates in the proximal direction relative to the case, hooks on the interlock sleeve abut the resilient arms on the latch tube and prevent the resilient arms from deflecting. The resilient arms prevent the drive carriage from abutting the latch tube. When the interlock sleeve translates in the distal direction relative to the case, the hooks on the interlock sleeve disengage the resilient arms on the latch tube, the resilient arms deflect and the drive carriage engages the latch tube.

In an exemplary embodiment, the autoinjector further comprises a slider movably arranged on the case. The slider includes an internal boss adapted to engage the drive carriage.

In an exemplary embodiment, the autoinjector further comprises a case release pin slidably disposed in the case. The pin (30) has an outer surface adapted to engage the slider and an inner surface adapted to engage a latch arm in the case. Movement of the slider causes movement of the pin to disengage the latch arm from the case.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 13A-B shows an exemplary embodiment of an autoinjector when replacing a used syringe.

Corresponding parts are marked with the same reference symbols in all figures.

DETAILED DESCRIPTION

Figure 1A:
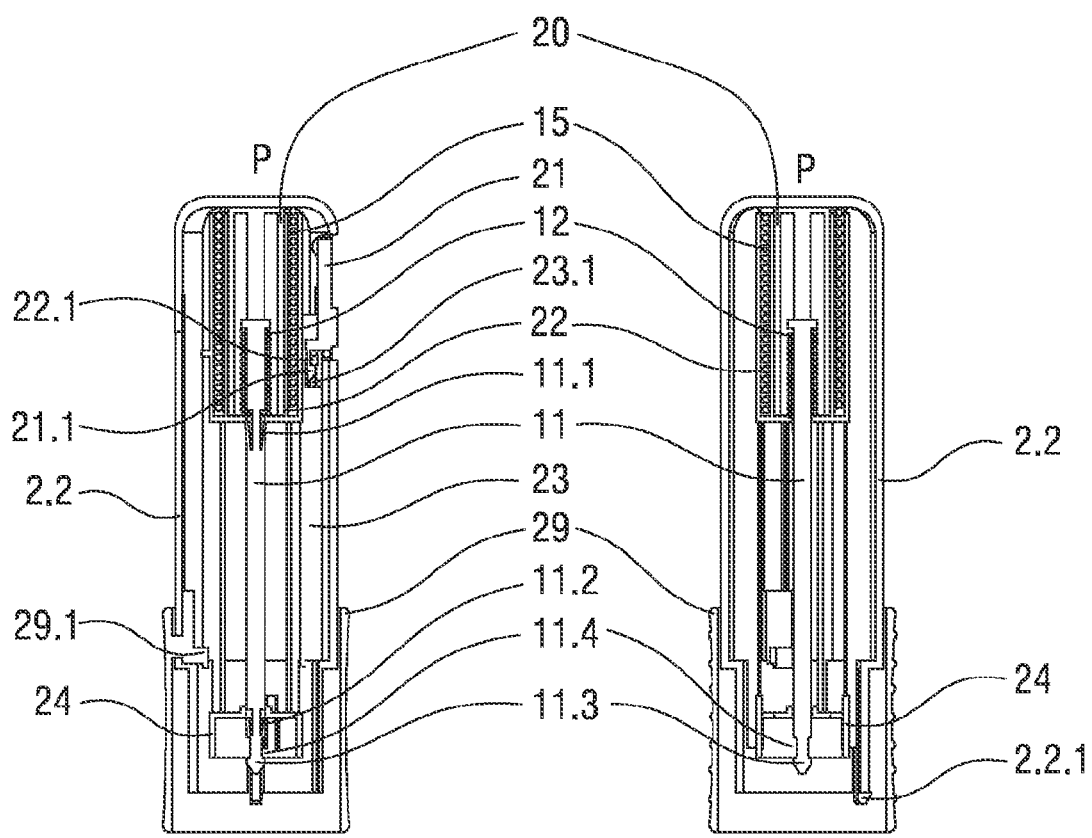
FIGS. 1A-B shows two longitudinal sections of an exemplary embodiment of an autoinjector according to the present invention.
Figure 1B:
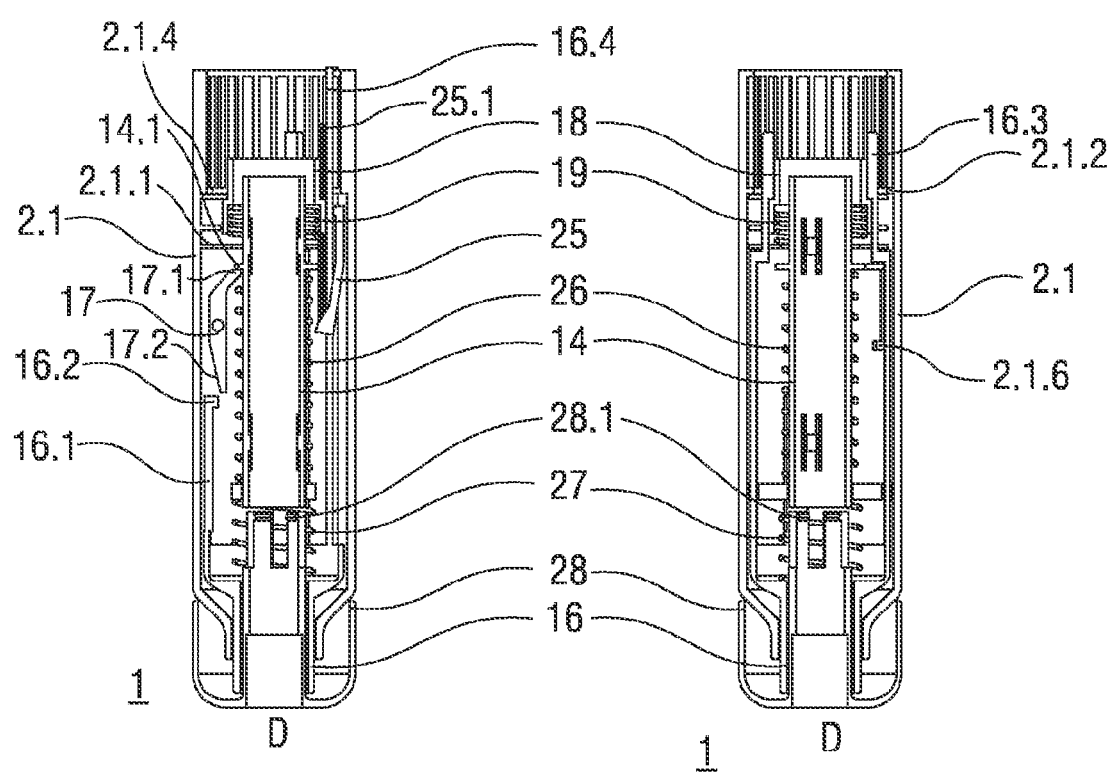

FIGS. 1A and 1B show two longitudinal sections of an exemplary embodiment of an autoinjector 1 in different section planes. The autoinjector 1 comprises an elongate housing having a front case 2.1 and a rear case 2.2 which may be separated. While the exemplary embodiment shown in FIGS. 1A and 1B shows the front and rear cases 2.1, 2.2 as being completely separable, in other exemplary embodiments, the cases 2.1, 2.2 may be hingedly coupled together. In another exemplary embodiment, the cases 2.1, 2.2 may be separable along a longitudinal axis of the housing, as opposed to a transverse axis of the housing.

In an exemplary embodiment, the front case 2.1 includes a carrier 14 adapted to hold a syringe. The carrier 14 is axially movable relative to the front case 2.1 and is biased toward a proximal direction P by a carrier spring 26 which bears proximally against a shoulder 14.1 on the carrier 14 and distally against a ledge formed in a distal portion of the front case 2.1.

The front case 2.1 also includes an interlock sleeve 16. The interlock sleeve 16 is axially movable relative to the front case 2.1 and is biased toward a distal direction D by a sleeve spring 27 which bears proximally against the ledge in the distal portion of the front case 2.1 and distally against the interlock sleeve 16. The interlock sleeve 16 is adapted to project distally through a distal opening in the front case 2.1, such that the interlock sleeve 16 contacts an injection site during an injection procedure, as explained further below.

The front case 2.1 also includes a latch sleeve 18 adapted to ensure that the front case 2.1 and the rear case 2.2 remain engaged during an injection procedure, as described further below. The latch sleeve 18 is axially movable relative to the front case 2.1 and is biased toward the proximal direction P by a latch sleeve spring 19 which bears proximally against the latch sleeve 18 and distally against a third rib 2.1.1 formed in a proximal portion of the front case 2.1. Hooks 16.3 on a proximal end of the interlock sleeve 16 are adapted to engage a shoulder formed on the latch sleeve 18. The hooks 16.3 limit extension of the interlock sleeve 16 relative to the front case 2.1, because the latch sleeve spring 19 requires more force to compress it than the sleeve spring 27. Further, a fourth rib 2.1.4 formed on the first case 2.1 abuts the latch sleeve 18 and prevents the latch sleeve 18 from moving proximally relative to the front case 2.1.

In an exemplary embodiment, the autoinjector 1 includes one or more latch mechanisms for preventing inadvertent actuation of the autoinjector 1. A first latch mechanism is adapted to prevent movement of the carrier 14 relative to the front case 2.1 prior to retraction of the interlock sleeve 16. In an exemplary embodiment, the first latch mechanism comprises a syringe backwards latch 17 pivotably coupled to a peg on the front case 2.1. A proximal nose 17.1 of the syringe backwards latch 17 is adapted to engage the shoulder 14.1 on the carrier 14. A distal ramp 17.2 of the syringe backwards latch 17 is adapted to engage a first arm 16.1 extending proximally from the interlock sleeve 16. A proximal end of the first arm 16.1 may include a protrusion 16.2 adapted to engage the distal ramp 17.2. As explained further below, when the interlock sleeve 16 is retracted in the proximal direction P relative to the front case 2.1, the first arm 16.1 engages the distal ramp 17.2, the syringe backwards latch 17 pivots and the proximal nose 17.1 disengages the shoulder 14.1, allowing the carrier 14 to move axially in the distal direction D relative to the front case 2.1. In an exemplary embodiment, a latch spring (not shown) may bias the syringe backwards latch 17 in an angular position in which the nose 17.1 engages the shoulder 14.1.

In another exemplary embodiment the syringe backwards latch 17 may have a straight end instead of the ramp 17.2 in which case a ramp may be provided at the protrusion 16.2. In yet another exemplary embodiment both the syringe backwards latch 17 and the protrusion 16.2 may have corresponding ramped surfaces.

In an exemplary embodiment, the front case 2.1 includes a second latch mechanism for preventing movement of the carrier 14 in the proximal direction P after the injection procedure. The second latch mechanism may include a resilient syringe forward latch 25 which deflects when it is engaged by the shoulder 14.1 as the carrier 14 moves axially in the distal direction D. When, under force of the carrier spring 26, the carrier 14 moves in the proximal direction P, the shoulder 14.1 abuts the syringe forward latch 25 which has returned to its non-deflected position. The latch 25 may include a lever 25.1 which can be pressed manually to re-deflect the syringe forward latch 25 when resetting the autoinjector 1, as explained further below.

In an exemplary embodiment, the rear case 2.2 comprises a drive spring 15 adapted to apply a force to a plunger on a syringe in the autoinjector 1. The drive spring 15 is arranged on a fixed sleeve 20 which is coupled to a proximal end of the rear case 2.2. The drive spring 15 bears proximally on the rear case 2.2 and distally on a drive carriage 22 which is arranged telescopically on the fixed sleeve 20. The drive carriage 22 is adapted to move axially relative to the rear case 2.2.

In an exemplary embodiment, a plunger 11 is coupled to the drive carriage 22 so that the plunger 11 may be pushed in the distal direction D by the drive spring 15. A proximal end of the plunger 11 extends into the drive carriage 22. A plunger spring 12 is arranged within the drive carriage 22 between the distal end of the plunger 11 and the drive carriage 22 and is arranged to bias the plunger 11 against the drive carriage 22. At least one radially biased, proximal resilient arm 11.1 on the plunger 11 abuts the drive carriage 22 and prevents the plunger 11 from translating axially relative under the force of the plunger spring 12.

A distal end of the plunger 11 is coupled to a latch tube 24 which is adapted to engage the latch sleeve 18 when the front case 2.1 and rear case 2.2 are assembled. At least one radially biased, distal resilient arm 11.2 on the plunger 11 abuts the latch tube 24 and prevents the plunger 11 from translating axially relative to the latch tube 24. The latch tube 24 includes proximally directed resilient arms 24.1.

A coupling head 11.3 having an indent 11.4 is formed at the distal end of the plunger 11. The coupling head 11.3 is adapted to releasably engage a syringe, as explained further below.

In an exemplary embodiment, a trigger button 21 is arranged on the rear case 2.2. The trigger button 21 may be disposed on a lateral surface of the rear case 2.2 or a proximal end of the rear case 2.2. The trigger button 21 may include a catch arm 21.1 adapted to engage a catch 22.1 on the drive carriage 22, preventing axial movement of the drive carriage 22 in the distal direction D. When the trigger button 21 is pressed, the catch arm 21.1 disengages the catch 22.1, allowing the drive carriage 22 to be propelled in the distal direction D by the force of the drive spring 15.

In an exemplary embodiment, the rear case 2.2 includes a third latch mechanism for preventing inadvertent actuation of the autoinjector 1. The third latch mechanism is adapted to prevent movement of the trigger button 21 prior to retraction of the interlock sleeve 16 into the front case 2.1. In an exemplary embodiment, the third latch mechanism comprises a trigger lockout bar 23 axially movable relative to the rear case 2.2, operably coupled to the interlock sleeve 16, and adapted to engage the trigger button 21. The trigger lockout bar 23 may be biased (e.g., by a spring, not shown) in a position abutting and preventing movement of the trigger button 21 relative to the rear case 2.2. Refraction of the interlock sleeve 16 relative to the front case 2.1 may displace the trigger lockout bar 23 in the proximal direction P, and align a recess 23.1 on the trigger lockout bar 23 with the trigger button 21. The trigger button 21 can then be pressed and received by the recess 23.1.

In an exemplary embodiment, a second arm 16.4 extending proximally from the interlock sleeve 16 may engage the trigger lockout bar 23 when the front case 2.1 is coupled to the rear case 2.2. When the interlock sleeve 16 is refracted into the front case 2.1, the second arm 16.4 may push the trigger lockout bar 23 in the proximal direction P relative to the rear case 2.2 to align the recess 23.1 with the trigger button 21.

In an exemplary embodiment, the autoinjector 1 includes a locking mechanism for locking the front case 2.1 and the rear case 2.2 in a coaxial position. In an exemplary embodiment, the locking mechanism comprises two resilient latch arms 2.2.1 extending distally from the rear case 2.2 and adapted to engage a first rib 2.1.2 in the front case 2.1, as explained further below. The locking mechanism may further include a slider 29 movably mounted on the rear case 2.2. The slider 29 may be spring-loaded and biased in the distal direction D (or a lock position). An internal boss 29.1 on the slider 29 may be adapted to engage the drive carriage 22 when the slider 29 is moved from the lock position proximally to an unlock position. Movement of the slider 29 and the drive carriage 22 in the proximal direction may re-compress the drive spring 15 for subsequent use.

A protective cap 28 may be attached to a distal end of the front case 2.1. The cap 28 may include resilient barbs 28.1 adapted to engage a needle sheath on a needle of a syringe in the autoinjector 1.

In figures 1A and 1B the front case 2.1 and rear case 2.2 are separate, and a syringe has not yet been inserted.

Figures 2A, 2B:
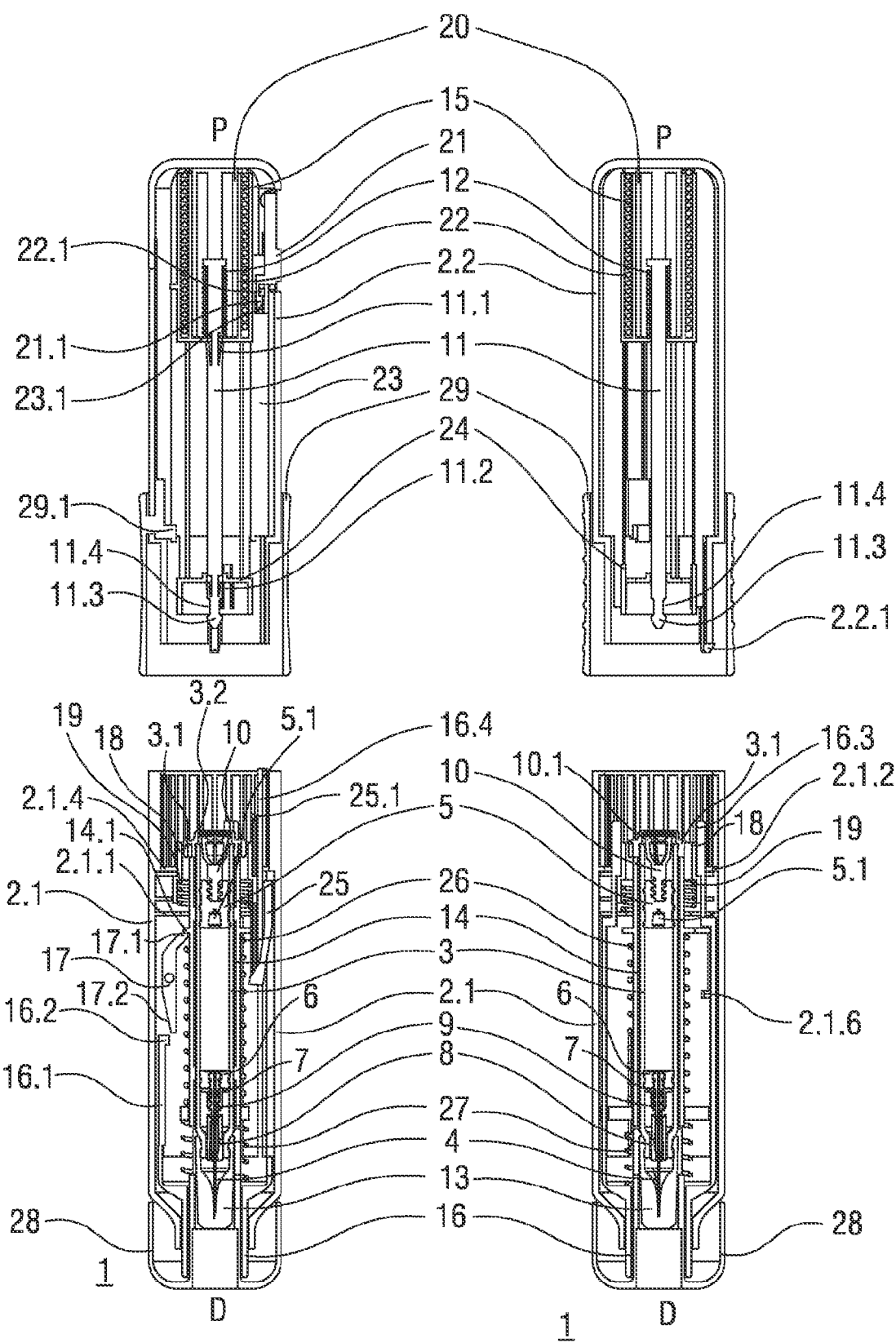
FIGS. 2A-B shows an exemplary embodiment of an autoinjector during insertion of a syringe.

FIGS. 2A and 2B show the front case 2.1 and rear case 2.2 still separate but with a syringe 3 inserted into the carrier 14.

The syringe 3 may be inserted into the carrier 14 until a finger flange 3.1 on the syringe 3 abuts a proximal end of the carrier 14.

In an exemplary embodiment, the syringe 3 may have a needle retraction mechanism. The syringe 3 may include a barrel, a stopper 5 slidably arranged within the barrel, and a needle 4 arranged on a distal end of the syringe 3. The syringe 3 may include a needle retraction mechanism comprising a needle seal 6 slidably arranged in a distal end of the barrel, an ejector ring 7 distal of the needle seal 6, a needle retainer 8 arranged on the distal end of the syringe 3 and adapted to engage a needle mount 9 coupled to the needle 4. The stopper 5 includes a cavity 5.1 adapted to engage the needle mount 9, as described in more detail below.

In the exemplary embodiment, the syringe 3 includes a plunger coupling 10 coupled to the stopper 5 and adapted to engage the plunger 11. The plunger coupling 10 comprises one or more resilient coupling arms 10.1 adapted to releasably engage the coupling head 11.3 of the plunger 11. The coupling arms 10.1 may have hooks which are adapted to engage the indents 11.4 in the coupling head 11.3.

When the syringe 3 is assembled a needle sheath 13 is attached to the needle 4.

Figures 3A, 3B:
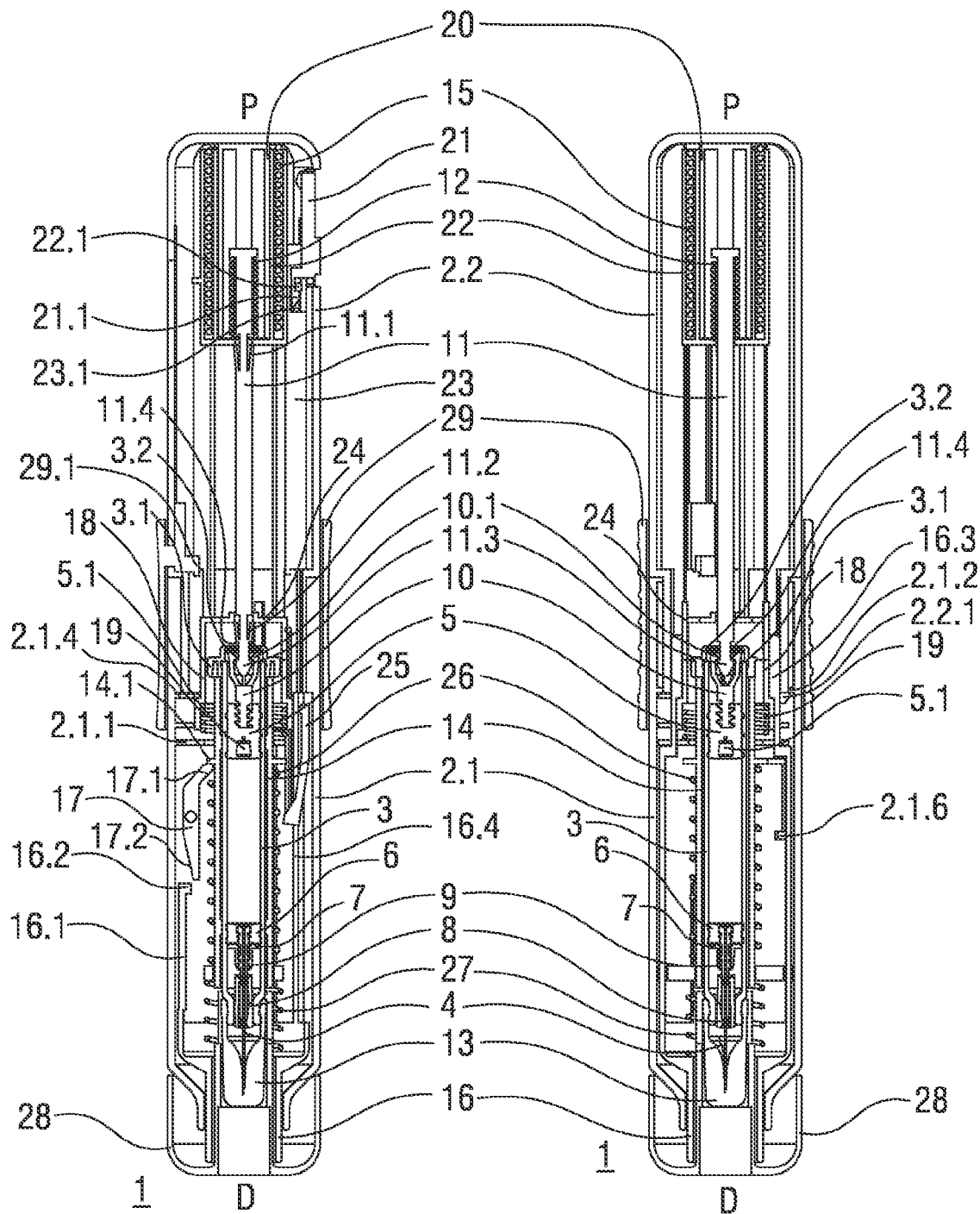
FIGS. 3A-B shows an exemplary embodiment of an autoinjector when assembled.

As shown in FIGS. 3A and 3B, once the syringe 3 is placed in the carrier 14, the front case 2.1 may be coupled to the rear case 2.2 when the latch arms 2.2.1 on the rear case 2.2 engage the first rib 2.1.2 in the front case 2.1. The coupling head 11.3 on the plunger 11 passes through the resilient coupling arms 10.1 deflecting them radially, and when the indent 11.4 is aligned with the hooks on the coupling arms 10.1, the plunger coupling 10 engages the plunger 11. In an exemplary embodiment, a viewing window may be disposed in the front case 2.1, the rear case 2.2 and/or the slider 29 which allows the user to visualize the connection of the plunger 11 and the plunger coupling 10. For example, the plunger coupling 10 may be a first color (e.g., yellow) and the coupling head 11.3 of the plunger 11 may a second color (e.g., blue), and the user may be instructed to refrain from activating the autoinjector 1 until the second color is visible through the viewing window.

The latch tube 24, proximally bearing against a rib (not shown) in the rear case 2.2, distally abuts the latch sleeve 18 and is kept in a proximal position by the force of the latch sleeve spring 19. In an exemplary embodiment, a feedback (e.g., an audible click) may be provided when the latch arms 2.2.1 engage the first rib 2.1.2 to notify the user that the front case 2.1 is secured to the rear case 2.2. The latch arms 2.2.1 and the first rib 2.1.2 may have corresponding ramped surfaces to facilitated engagement/disengagement. As shown in FIG. 3B, the latch arms 2.2.1 are maintained in engagement with the first rib 2.1.2, because the latch arms 2.2.1 abut the hooks 16.3 and the hooks 16.3 abut the latch sleeve 18. The slider 29 may be in an extended position, covering a joint between the front and rear cases 2.1, 2.2.

Figure 4:
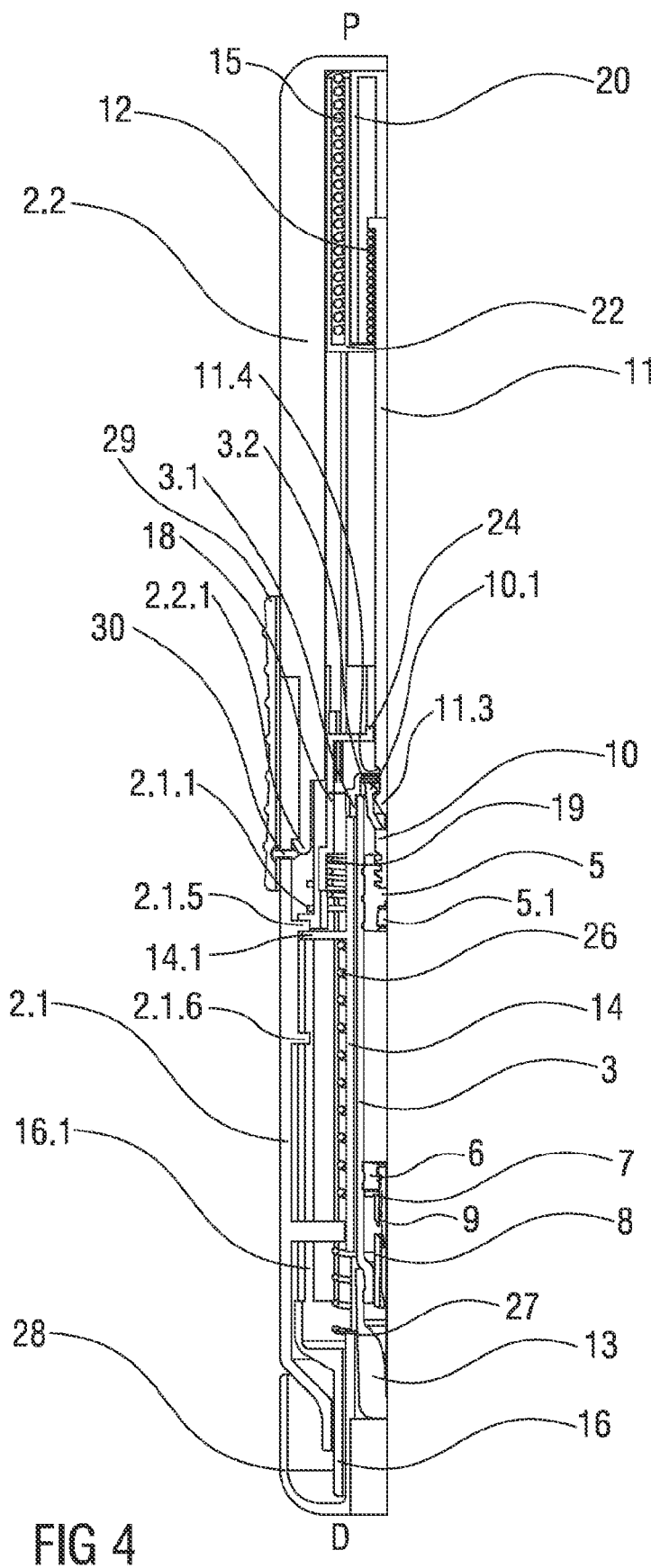
FIG. 4 is a longitudinal section in the situation as in FIG. 3 in another section plane.

FIG. 4 shows a longitudinal section of an exemplary embodiment of the autoinjector 1. In this exemplary embodiment, the front case 2.1 includes a biased case release pin 30. The case release pin 30 has an inner ramped surface which is adapted to engage the latch arm 2.2.1 and an outer ramped surface which is adapted to engage a cavity formed in the slider 29. When the front case 2.1 and the rear case 2.2 are connected and the slider 29 is translated to lock the cases together, the case release pin 30 extends through an aperture in the front case 2.1 and the inner ramped surface abuts the latch arm 2.2.1 and the outer ramped surface engages the cavity in the slider 29. When the slider 29 is translated in the proximal direction P, the slider 29 pushes the outer ramped surface which translates the case release pin 30 transversely and causes the inner ramped surface to radially deflect the latch arm 2.2.1 to disengage the first rib 2.1.2.

Figures 5A, 5B:
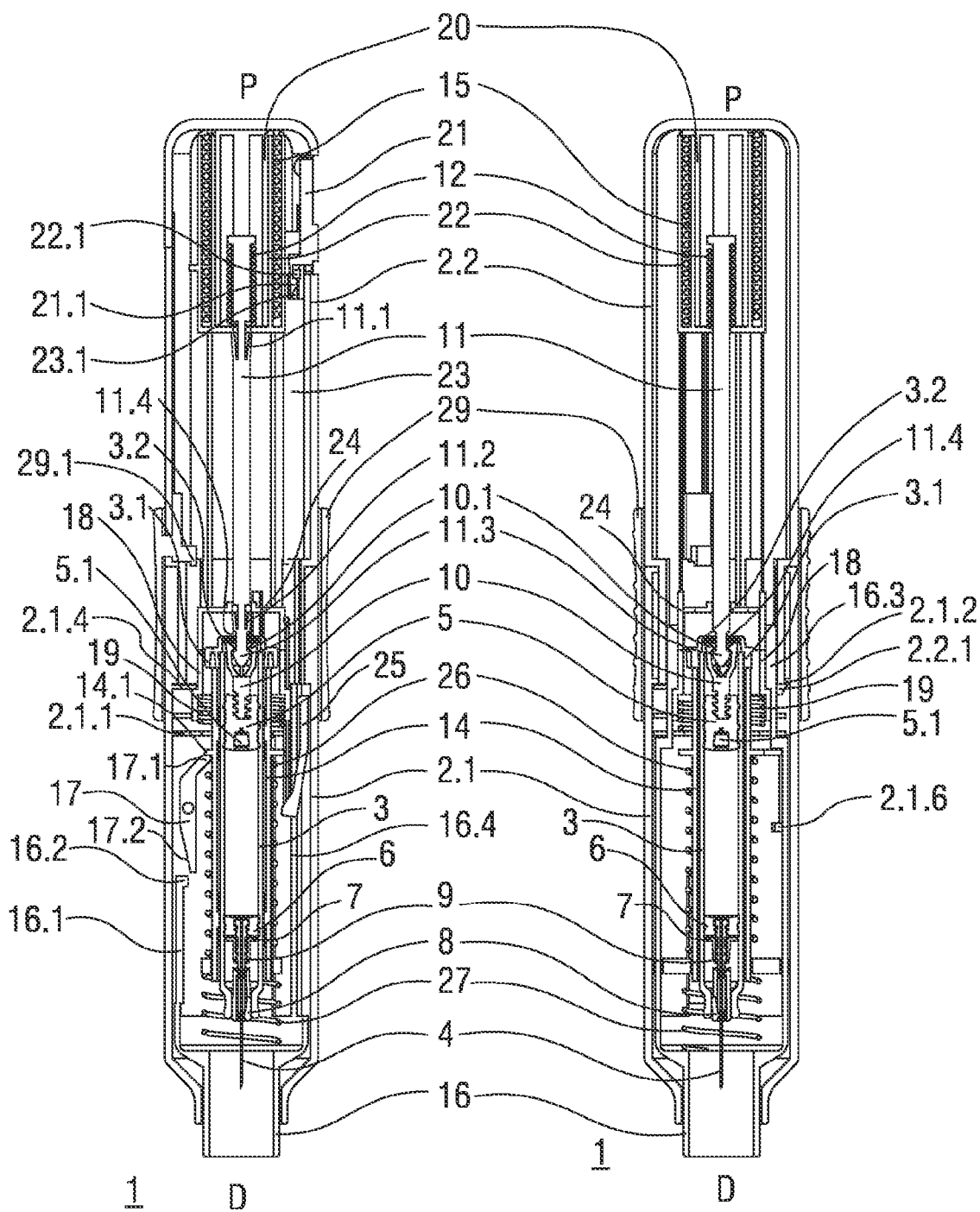
FIG. 5A-B shows an exemplary embodiment of an autoinjector after removal of a cap.

In FIGS. 5A and 5B, the cap 28 has been removed from the autoinjector 1. When the cap 28 is removed (e.g., by pulling in the distal direction D), the barbs 28.1 on the cap 28 engage the needle sheath 13 and remove the needle sheath 13 with the cap 28. Once the cap 28 is removed, the barbs 28.1 are no longer constrained so the protective needle sheath 13 is released and may be easily removed from the cap 28. For example, the barbs 28.1 may be biased radially away from the longitudinal axis of the autoinjector 1. When coupled to the autoinjector 1, the barbs 28.1 may be deflected and constrained by the distal end of the interlock sleeve 16. Thus, when the cap 28 is separated from the autoinjector 1, the barbs 28.1 may return to their non-deflected position and release the needle sheath 13.

When the cap 28 is removed from the autoinjector 1, the interlock sleeve 16 is in an extended position, protruding from the distal opening of the front case 2.1.

Figures 6A, 6B:
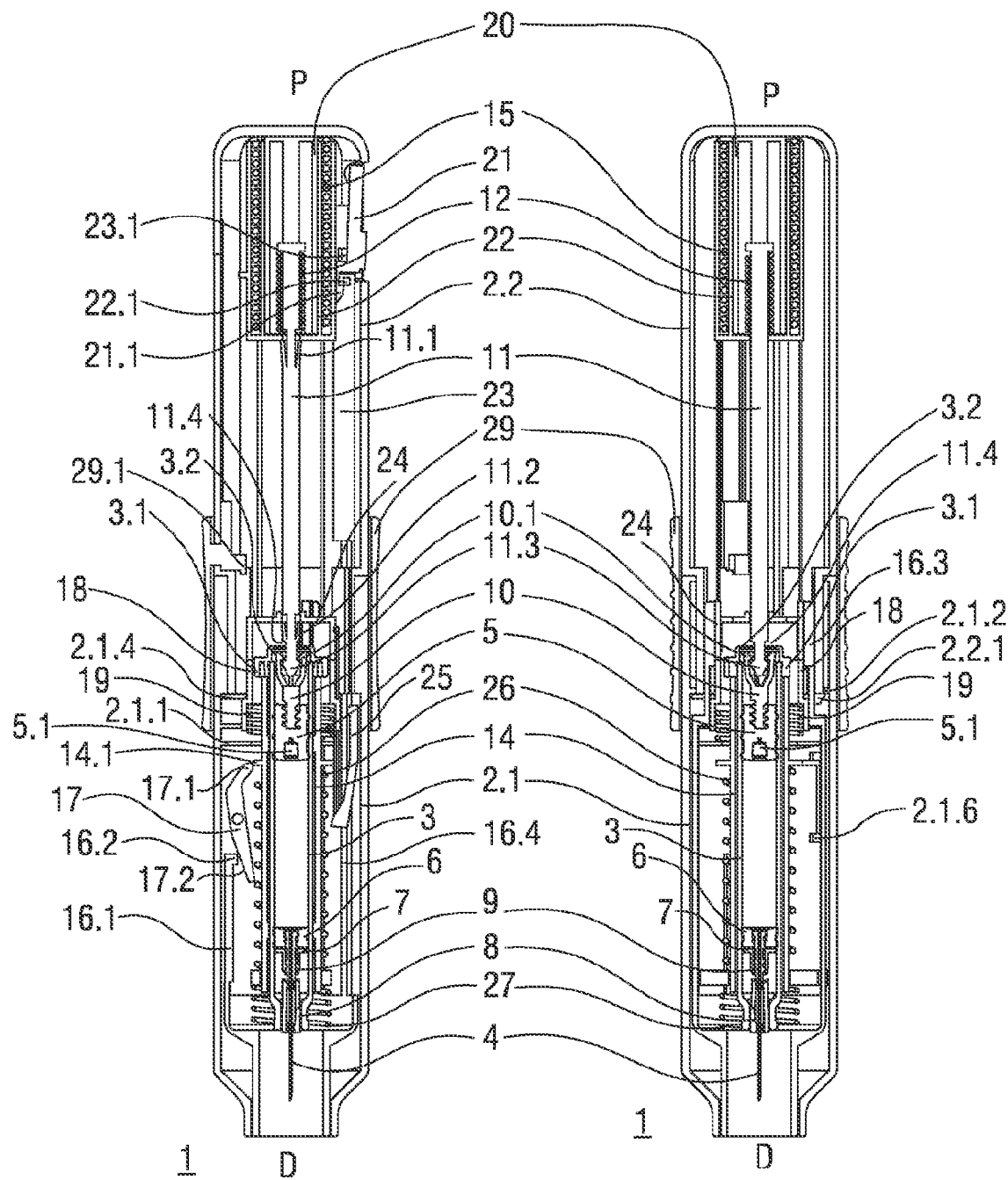
FIG. 6A-B shows an exemplary embodiment of an autoinjector pressed against an injection site.

In FIGS. 6A and 6B, the interlock sleeve 16 is in a retracted position relative to the front case 2.1, because the autoinjector 1 has been pressed against an injection site. As the interlock sleeve 16 translates in the proximal direction P relative to the front case 2.1, the first arm 16.1 engages the distal ramp 17.2 of the syringe backward latch 17, causing the syringe backward latch 17 to rotate and the nose 17.1 to disengage the shoulder 14.1 on the carrier 14. Also, the second arm 16.4 engages the trigger lockout bar 23 and pushes the trigger lockout bar 23 in the proximal direction P relative to the rear case 2.2. When the trigger lockout bar 23 moves proximally relative to the rear case 2.2, the recess 23.1 is aligned with the trigger button 21. The autoinjector 1 can now be activated by pressing the trigger button 21.

Translation of the interlock sleeve 16 in the proximal direction P also moves the proximal end of the interlock sleeve 16 behind the latch arms 2.2.1 on the rear case 2.2, which further reinforces the engagement of the latch arms 2.2.1 and the first rib 2.1.2 on the front case 2.1. The hooks 16.3 on the interlock sleeve 16 disengage the shoulder on the latch sleeve 18. However the latch sleeve 18 remains in position relative to the front case 2.1, because the shoulder on the latch sleeve 18 abuts the fourth rib 2.1.4.

Figures 7A, 7B:
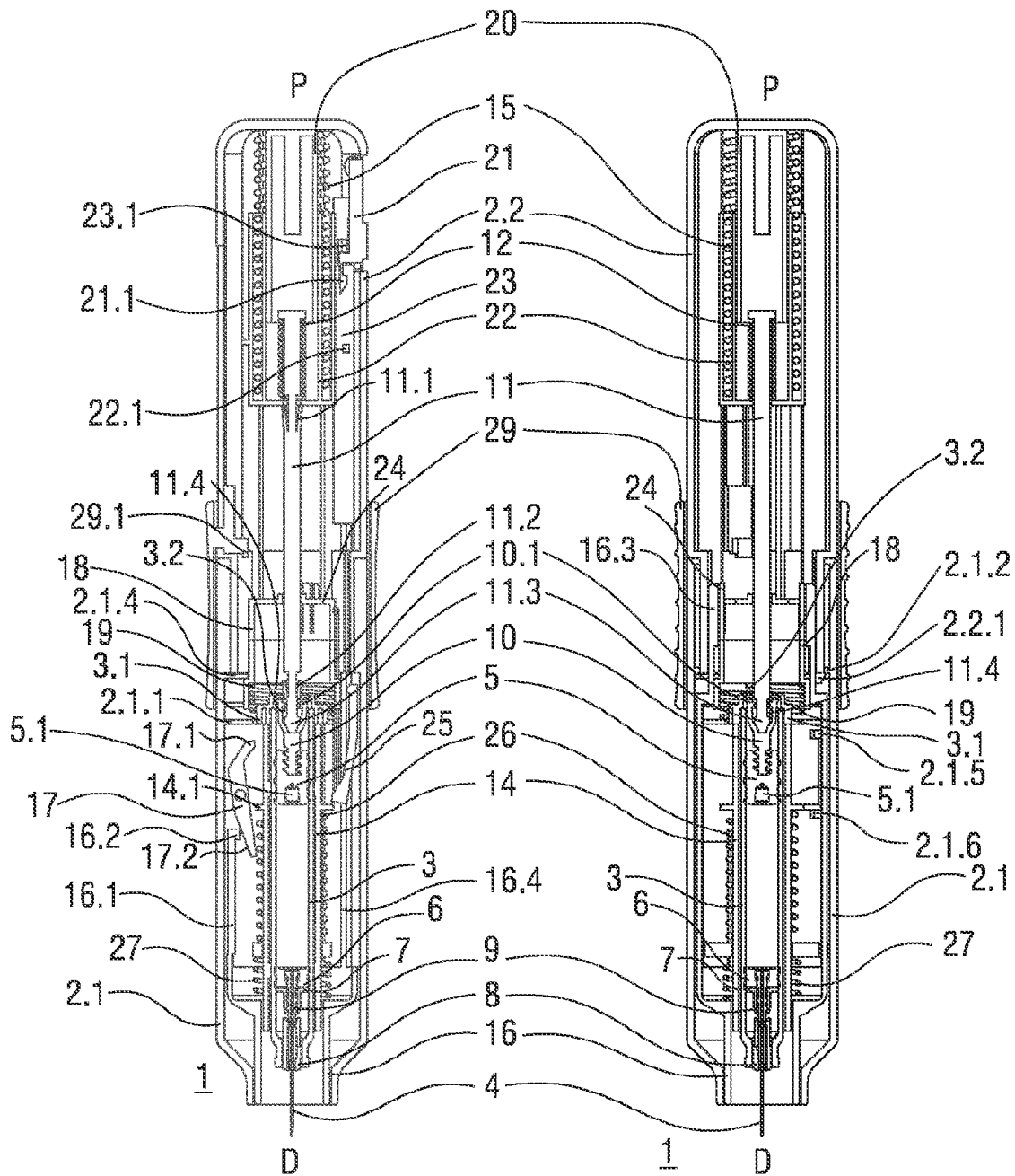
FIG. 7A-B shows an exemplary embodiment of an autoinjector with a needle extending from a distal end.

As shown in FIGS. 7A and 7B, when the trigger button 21 is pressed, the catch arm 21.1 on the trigger button 21 disengages the catch 22.1 and releases the drive carriage 22. The force from the expansion of the drive spring 15 pushes the drive carriage 22 in the distal direction D. Because the carrier 14 is not fixed relative to the front case 2.1, when the drive carriage 22 engages the first resilient arms 11.1 on the plunger 11, the force of the drive spring 15 is propagated through the plunger 11, plunger coupling 10, the stopper 5 and the syringe 3 to the carrier 14 so as to displace it axially in the distal direction D relative to the front case 2.1 for needle insertion. Because friction opposing relative motion of the stopper 5 and the barrel is greater than the sum of the forces required to compress the carrier spring 26 and to insert the needle 4 into the injection site, the needle 4 is inserted without dispensing any medicament from the syringe 3.

As the carrier 14 moves axially in the distal direction D relative to the front case 2.1, the shoulder 14.1 on the carrier 14 engages, and temporarily deflects, the syringe forward latch 25. When the shoulder 14.1 bypasses the syringe forward latch 25, the syringe forward latch 25 returns to its non-deflected position, as shown in FIG. 7A.

The carrier 14 continues moving axially in the distal direction D relative to the front case 2.1 until the finger flange 3.1 on the syringe 3 abuts the first rib 2.1.1 in the front case 2.1. Needle penetration depth can be varied by varying an axial location of the first rib 2.1.1. Once the finger flange 3.1 abuts the first rib 2.1.1, the force applied to the stopper 5 (from the drive spring 15) is sufficient to overcome friction and emptying of the syringe 3 commences.

In another exemplary embodiment, axial movement of the carrier 14 is limited by a fifth rib 2.1.5 and a sixth rib 2.1.6. For example, a flange on the carrier 14 may abut the fifth rib 2.1.5 to limit retraction of the carrier 14 relative to the front case 2.1 and may abut the sixth rib 2.1.6 to limit distally directed movement of the carrier 14 relative to the front case 2.1 (which may, in part, define an injection depth).

Figures 8A, 8B:
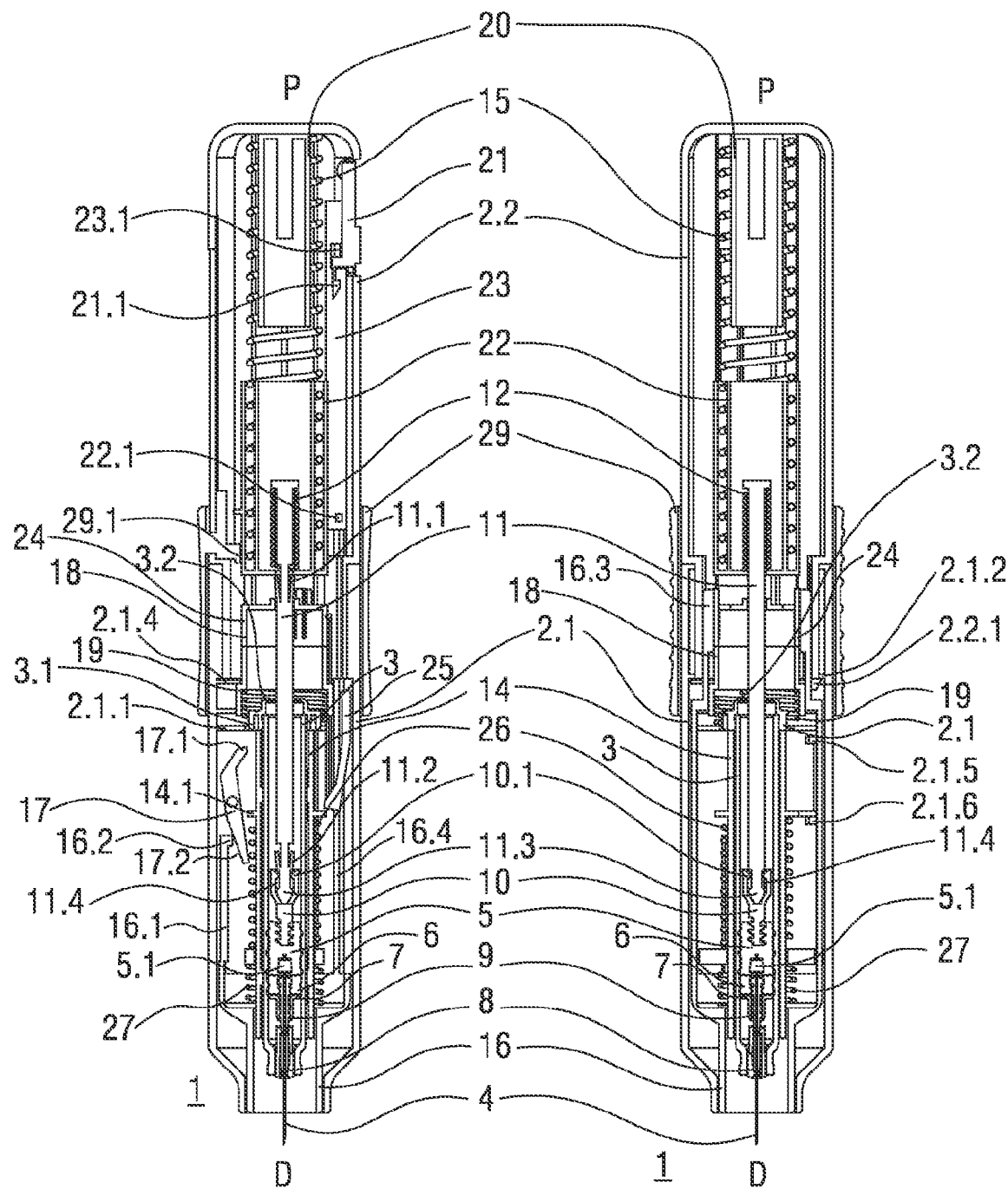
FIG. 8A-B shows an exemplary embodiment of an autoinjector near an end of dose.

FIGS. 8A and 8B show the autoinjector 1 when the syringe 3 is almost emptied. The stopper 5 has abutted the needle seal 6. As the stopper 5 advances further, it pushes the needle seal 6 and the ejector ring 7 in the distal direction D.

Figures 9A, 9B:
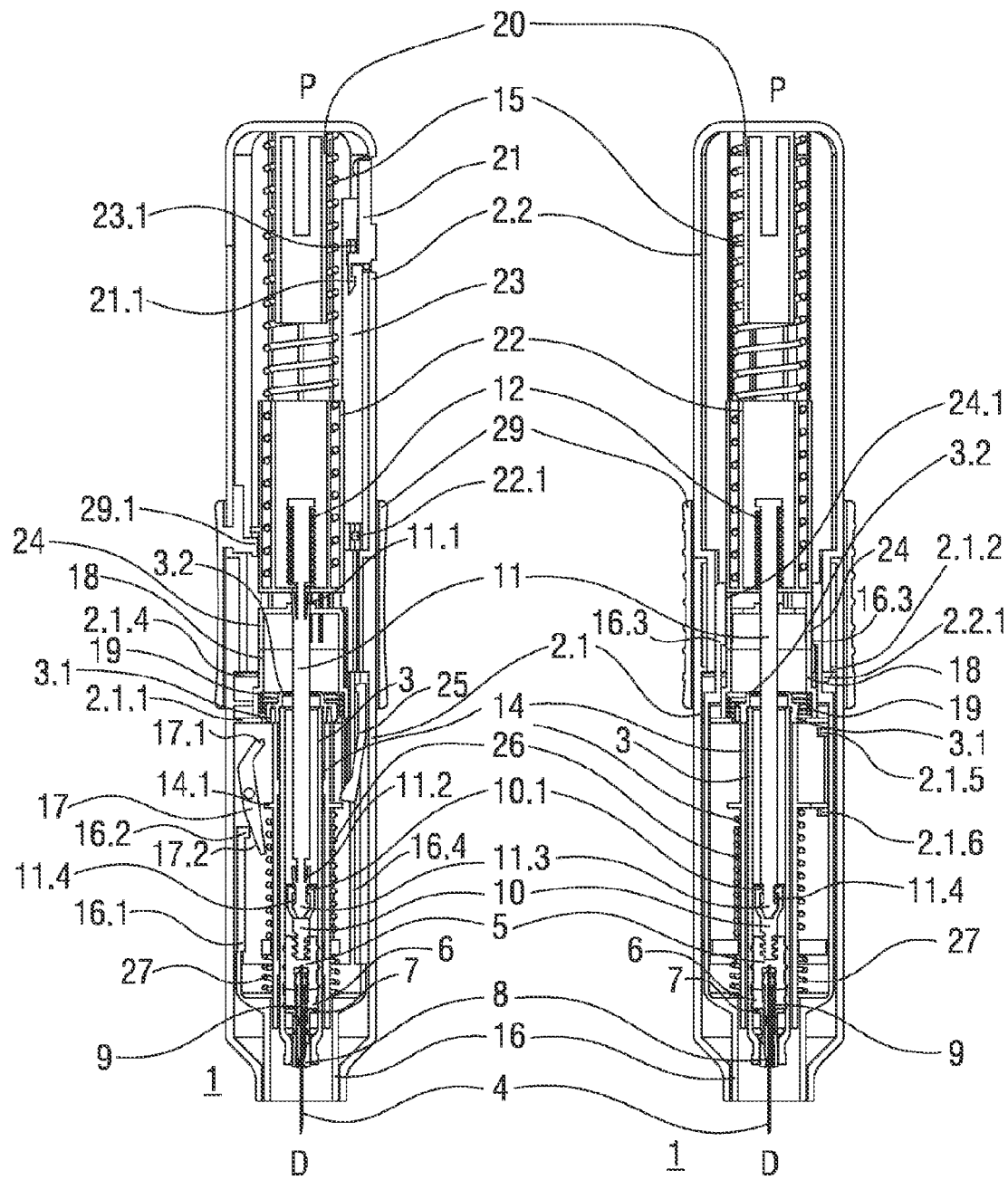
FIG. 9A-B shows an exemplary embodiment of an autoinjector at an end of dose.

As shown in FIGS. 9A and 9B, the drive carriage 22 abuts the resilient arms 24.1 of the latch tube 24 and pushes the latch tube 24 and the latch sleeve 18 in the distal direction D against the biasing force of the latch sleeve spring 19 until the latch sleeve 18 abuts the first rib 2.1.1. The resilient arms 24.1 on the latch tube 24 are prevented deflecting radially, because they abut the hooks 16.3 of the interlock sleeve 16. At the same time, the plunger 11 pushes the plunger coupling 10, the stopper 5 and the needle seal 6 into abutment with the ejector ring 7 which abuts the needle retainer 8. When the ejector ring 7 engages the needle retainer 8, ramped distal arms on the ejector ring 7 deflect ramped proximal retainer arms on the needle retainer 8, releasing the needle mount 9 from the needle retainer 8. Substantially simultaneously, a proximal end of the needle mount 9 engages (e.g., frictionally, snap-fit, etc.) the cavity 5.1 in the stopper 5.

Figures 10A, 10B:
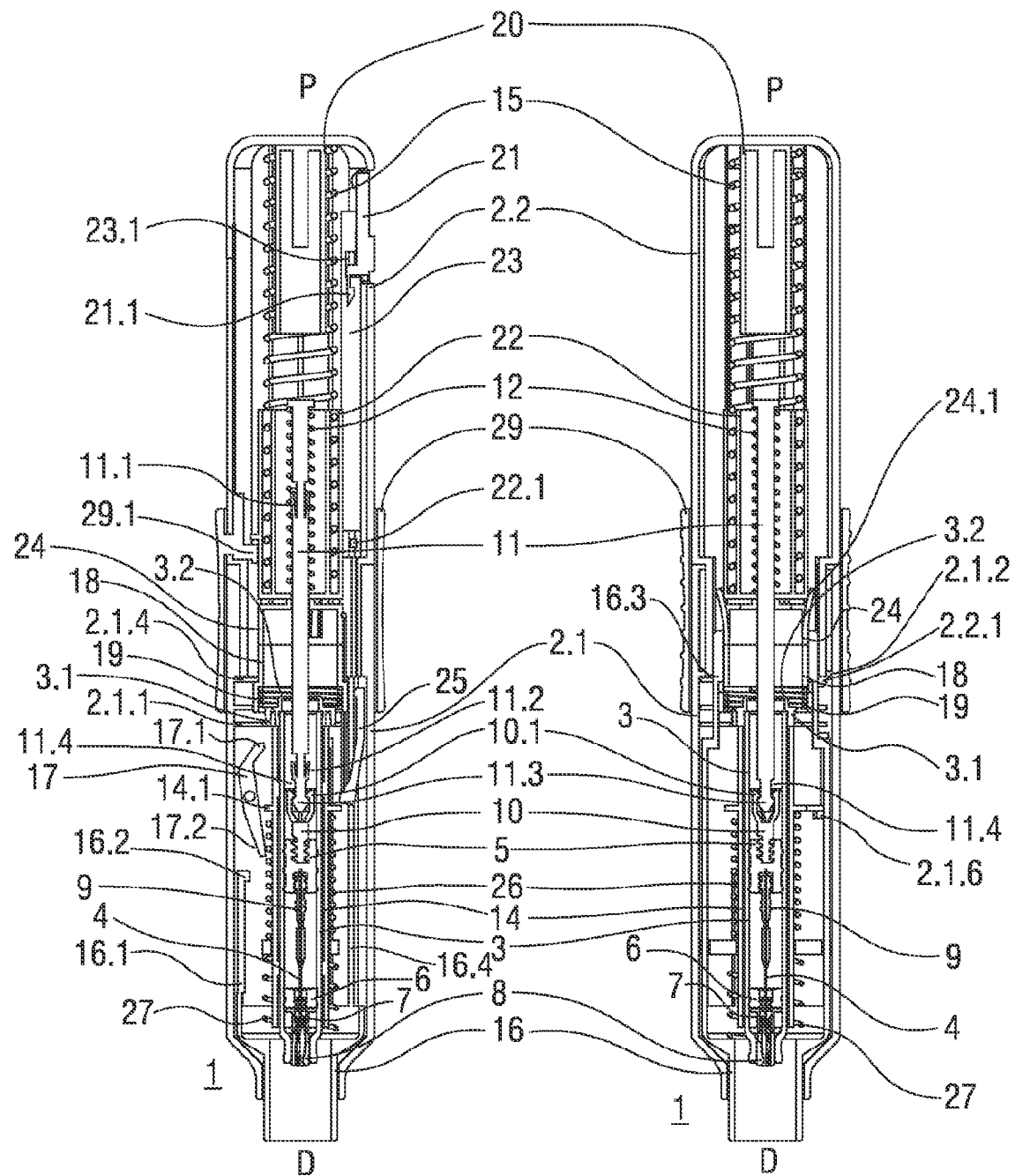
FIG. 10A-B shows an exemplary embodiment of an autoinjector after use.

As shown in FIGS. 10A and 10B, in an exemplary embodiment, when the autoinjector 1 is removed from the injection site, the interlock sleeve 16 translates in the distal direction D under the force of the sleeve spring 27 to ensure that the exposed needle 4 is covered. As the interlock sleeve 16 translates distally, the hooks 16.3 are displaced and no longer support the resilient arms 24.1 of the latch tube 24, which deflect radially under the force of the latch sleeve spring 19. The drive carriage 22 moves distally until it abuts the internal boss 29.1 on the slider 29. The proximal resilient arms 11.1 on the plunger 11 are deflected radially by a proximal opening in the latch tube 24 through which the plunger 11 passes. The proximal resilient arms 11.1 thus disengage the drive carriage 22, and the plunger spring 12 expands, forcing the plunger 11 in the proximal direction P through a distal opening in the drive carriage 22 and into the drive carriage 22. Given the engagement of the plunger 11 and the plunger coupling 10, movement of the plunger 11 in the proximal direction P causes corresponding movement of the plunger coupling 10, the stopper 5, the needle mount 9 and the needle 3, which is retracted into the barrel of the syringe 3.

Figures 11A, 11B:
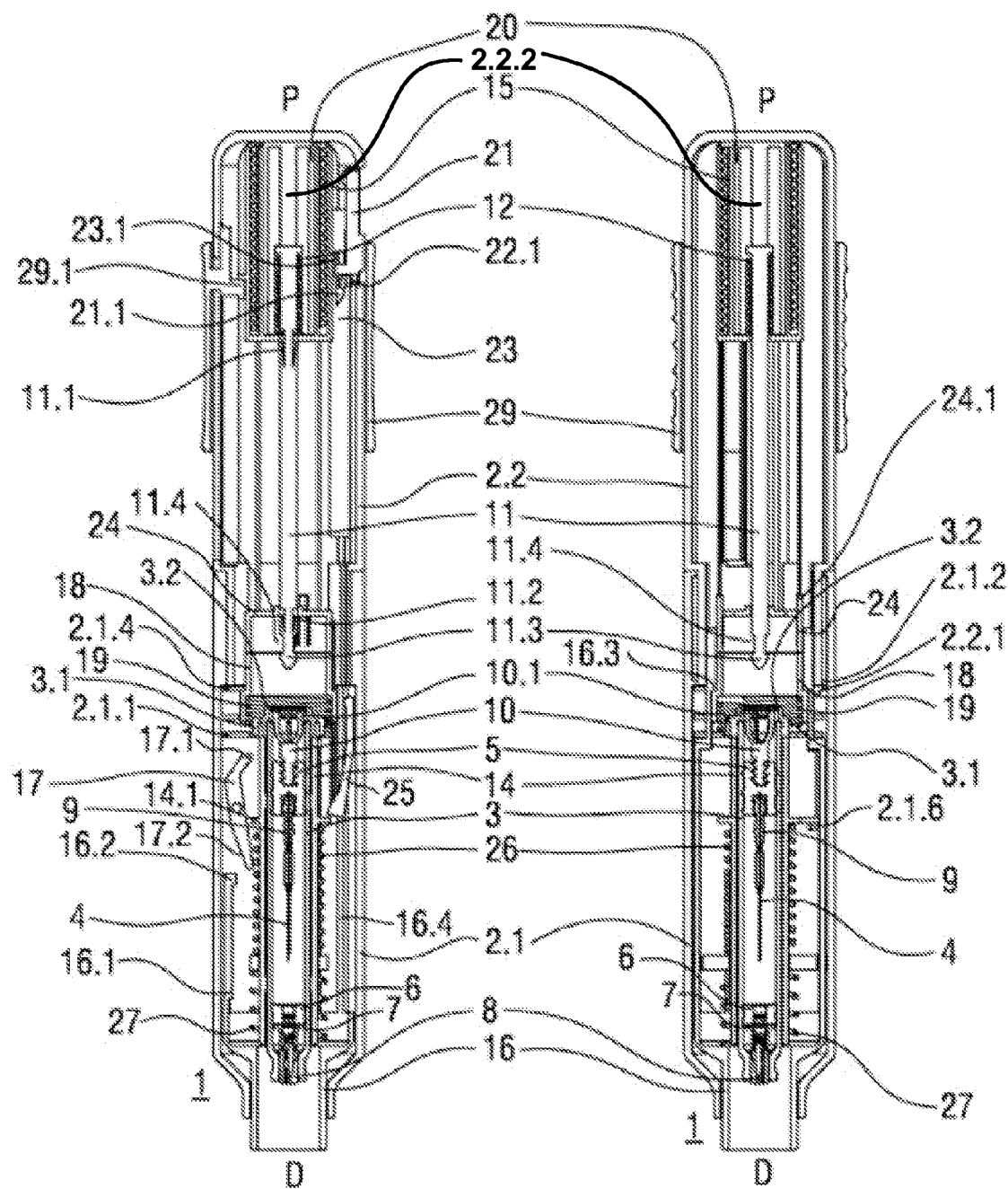
FIG. 11A-B shows an exemplary embodiment of an autoinjector with a sliding sleeve retracted for disassembling.

As shown in FIGS. 11A and 11B, the slider 29 is moved in the proximal direction P to reset the drive spring 15. When the slider 29 is moved proximally, it pushes the case release pin 30 transversely which disengages the latch arm 2.2.1 from the second rib 2.1.2, unlocking the front case 2.1 from the rear case 2.2.

The internal boss 29.1 on the resetting slider 29 engages the drive carriage 22 and slaves it in the proximal direction P as the slider 29 is translated thereby compressing the drive spring 15. As the drive carriage 22 moves in the proximal direction P, the catch 22.1 on the drive carriage 22 reengages the catch arm 21.1 on the trigger button 21. The retracting drive carriage 22, coupled to the plunger 11 through the plunger spring 12, pulls the plunger 11, plunger coupling 10, stopper 5 and needle 4 further in the proximal direction P.

As the plunger coupling 10 reaches the proximal end of the syringe 3, the resilient coupling arms 10.1 no longer outwardly supported. In an exemplary embodiment, proximal ends of the coupling arms 10.1 abut a release rib 3.2 on the finger flange 3.1 limiting further travel in the proximal direction P and causing the coupling arms 10.1 to deflect radially and disengage the coupling head 11.3 of the plunger 11.

As the plunger 11 continues translating in the proximal direction P, the distal resilient arms 11.2 re-engage the latch tube 24. The latch tube 24 and latch sleeve 18, no longer under load from the drive spring 15 have returned to their initial position in the proximal direction P driven by the latch spring 19 until the latch tube 24 proximally abuts the ridge in the rear case 2.2 thereby also stopping further translation of the plunger 11.

As the slider 29 still pulls on the drive carriage 22 in the proximal direction P, a proximal end of the plunger 11 abuts a stem 2.2.2 in the rear case 2.2 which prevents proximal movement of the plunger 11 as the slider 29 translates further proximally. Thus, the drive carriage 22 rides up the plunger 11, compressing the drive spring 15 and the plunger spring 12 until the proximal resilient arms 11.1 on the plunger 11 pass through the distal aperture in the drive carriage 22 and reengage the drive carriage 22. Hence, the plunger spring 12 is locked in the compressed state.

Figure 12A:
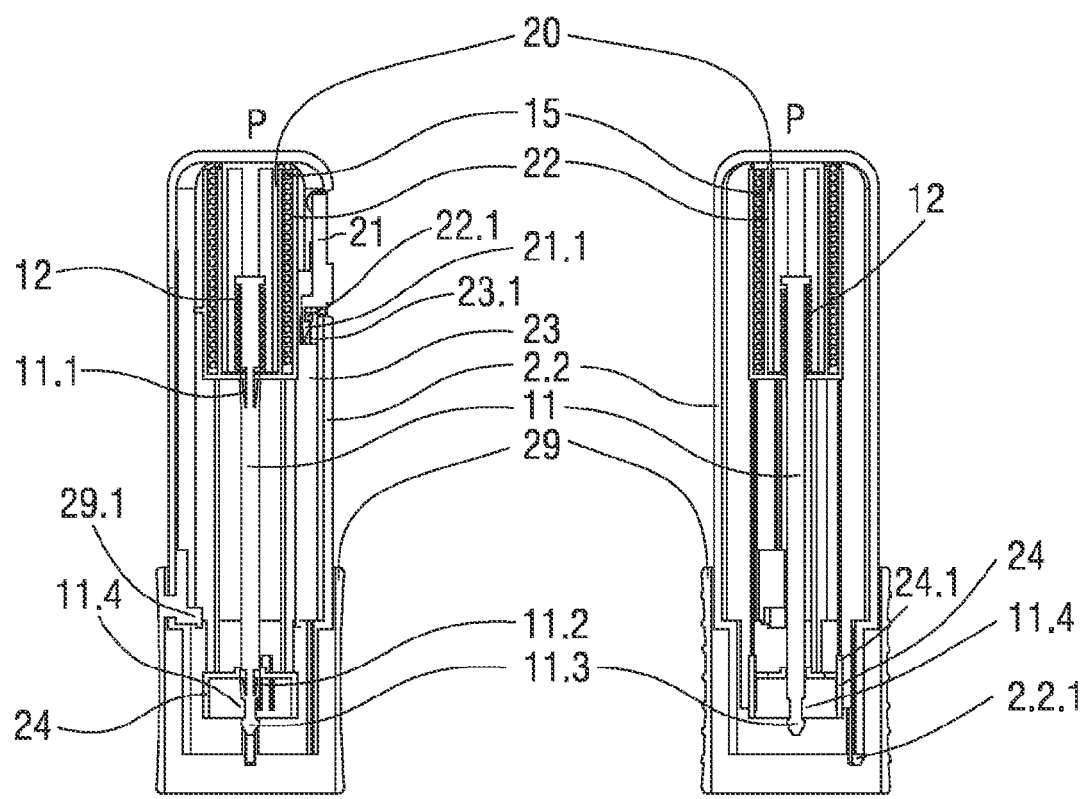
FIG. 12A-B shows an exemplary embodiment of a disassembled autoinjector.
Figure 12B:
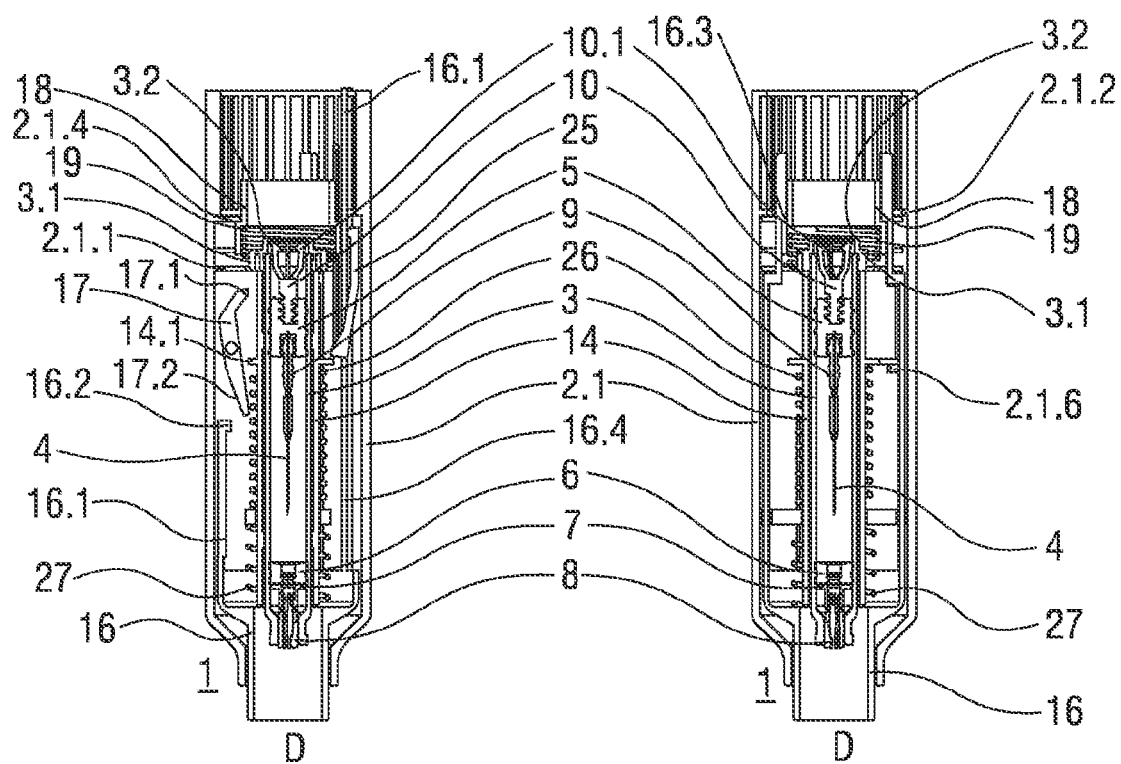

In FIGS. 12A and 12B, the syringe 3 is maintained in the advanced position due to the syringe forward latch arm 25 engaging the shoulder 14.1 on the carrier 14.

In FIGS. 13A and 13B, with the front and rear cases 2.1, 2.2 separated, the lever 25.1 connected to the syringe forwards latch 25 can be operated, e.g. by pushing the lever 25.1 in the distal direction D to deflect the syringe forwards latch 25 to disengage from the shoulder 14.1 on the carrier 14. The carrier spring 26, thus returns the carrier 14 and syringe 3 in the proximal direction P into their initial position. The user may now remove the syringe 3 from the carrier 14, and insert a new syringe.

As understood by those of skill in the art, while a syringe with a needle retraction mechanism has been described for use in the exemplary embodiments of the autoinjector 1, a syringe without any safety features (e.g., a Hypak syringe) may be used, and the autoinjector 1 may include one or more safety mechanisms, e.g., a locking mechanism for the interlock sleeve 16 to cover the needle 4.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B 30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl -ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl) -des(B30) human insulin and B29-N-(ω-carboxyheptadecanoyl) human insulin.

Exendin-4 for example means Exendin-4(1-39), a peptide of the sequence H-His -Gly-Glu-Gly-Thr-Phe-Thr-Ser-Asp-Leu-Ser-Lys-Gln-Met-Glu-Glu-Glu-Ala-Val-Arg-Leu-Phe -Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38[Met(O)14, Asp28] Exendin-4(1-39)-(Lys)6-N2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. An autoinjector comprising:
   a case;
   a drive carriage disposed in the case;
   a plunger coupled to the drive carriage, the plunger adapted to releasably engage a needle retraction mechanism in a syringe, wherein the plunger includes proximal resilient arms;
   a latch tube coupled to the plunger, the latch tube including resilient arms and a proximal aperture;
   wherein when the drive carriage abuts the latch tube, the proximal resilient arms of the plunger are deflected by the proximal aperture in the latch tube and the plunger translates in a proximal direction relative to the drive carriage under a force of a plunger spring,
   wherein when an interlock sleeve translates in a distal direction relative to the case, hooks on the interlock sleeve disengage the resilient arms on the latch tube, the resilient arms deflect and the drive carriage engages the latch tube,
   wherein translation of the drive carriage in the distal direction relative to the case causes the plunger to engage the needle retraction mechanism.

2. The autoinjector according to claim 1, further comprising:
   a drive spring biasing the drive carriage relative to the case.

3. The autoinjector according to claim 1, further comprising:
   the plunger spring biasing the plunger relative to the drive carriage.

4. The autoinjector according to claim 1, wherein the proximal resilient arms of the plunger are adapted to engage a distal aperture in the drive carriage.

5. The autoinjector according to claim 1, wherein the plunger includes distal resilient arms adapted to engage the proximal aperture in the latch tube.

6. The autoinjector according to claim 5, further comprising:
   a slider movably arranged on the case, wherein the slider includes an internal boss adapted to engage the drive carriage.

7. The autoinjector according to claim 6, further comprising:
   a case release pin slidably disposed in the case, the pin having an outer surface adapted to engage the slider and an inner surface adapted to engage a latch arm in the case, wherein movement of the slider causes movement of the pin to disengage the latch arm from the case.

8. The autoinjector according to claim 1, wherein the case includes a stem adapted to engage a proximal end of the plunger.

9. The autoinjector according to claim 1, wherein when the drive carriage separates from the latch tube, the drive carriage and the plunger translate in the proximal direction relative to the case until a stem engages a proximal end of the plunger and prevents the plunger from further translation while allowing further translation of the drive carriage, the further translation of the drive carriage causing the proximal resilient arms to deflect and re-engage a distal aperture of the drive carriage.

10. The autoinjector according to claim 1, further comprising:
    the interlock sleeve slidably disposed in the case; and a sleeve spring adapted to apply a biasing force to the interlock sleeve relative to the case.

11. The autoinjector according to claim 1, further comprising:
    a latch sleeve slidably disposed in the case; and
    a latch sleeve spring adapted to apply a biasing force to the latch sleeve relative to the case.

12. The autoinjector according to claim 1, wherein when the interlock sleeve translates in the proximal direction relative to the case, the hooks on the interlock sleeve abut the resilient arms on the latch tube and prevent the resilient arms from deflecting, the resilient arms preventing the drive carriage from abutting the latch tube.

* * * * *